US012685861B2

(12) United States Patent
Bradley et al.

(10) Patent No.: US 12,685,861 B2
(45) Date of Patent: Jul. 21, 2026

(54) INHALER TESTING APPARATUS

(71) Applicant: Copley Scientific Limited, Nottingham (GB)

(72) Inventors: Benjamin Bradley, Nottingham (GB); Mark Andrew Copley, Nottingham (GB)

(73) Assignee: Copley Scientific Limited, Nottingham (GB)

( * ) Notice: Subject to any disclaimer, the term of this patent is extended or adjusted under 35 U.S.C. 154(b) by 362 days.

(21) Appl. No.: 18/351,135

(22) Filed: Jul. 12, 2023

(65) Prior Publication Data

US 2024/0017055 A1 Jan. 18, 2024

(30) Foreign Application Priority Data

Jul. 14, 2022 (GB) ...................................... 2210357

(51) Int. Cl.
*A61M 99/00* (2012.01)
*A61M 15/00* (2006.01)

(52) U.S. Cl.
CPC ............. *A61M 99/00* (2022.08); *A61M 15/00* (2013.01); *A61M 2205/70* (2013.01); *A61M 2209/02* (2013.01)

(58) Field of Classification Search
CPC .............. A61M 99/00; A61M 2205/07; A61M 2205/071
See application file for complete search history.

(56) References Cited

U.S. PATENT DOCUMENTS

2020/0129711 A1 4/2020 Buck

FOREIGN PATENT DOCUMENTS

GB 2521148 A 6/2015
WO WO-2017112452 A1 * 6/2017 .......... A61M 15/009

OTHER PUBLICATIONS

Extended European Search Report, EP Patent Application No. 23184875.5, dated Nov. 21, 2023, pp. 1-8.
Search Report Under Section 17, GB Patent Application No. GB2210357.6, dated Jan. 16, 2023, p. 1.

* cited by examiner

*Primary Examiner* — Walter L Lindsay, Jr.
*Assistant Examiner* — Andrew V Do
(74) *Attorney, Agent, or Firm* — Bond Schoeneck & King, PLLC; Joseph M. Noto

(57) ABSTRACT

A volume and resistance compensator device; an inhaler testing apparatus containing the device; and methods for testing inhalers utilizing the device and apparatus for improving the consistency and reliability of the testing process are disclosed.

15 Claims, 6 Drawing Sheets

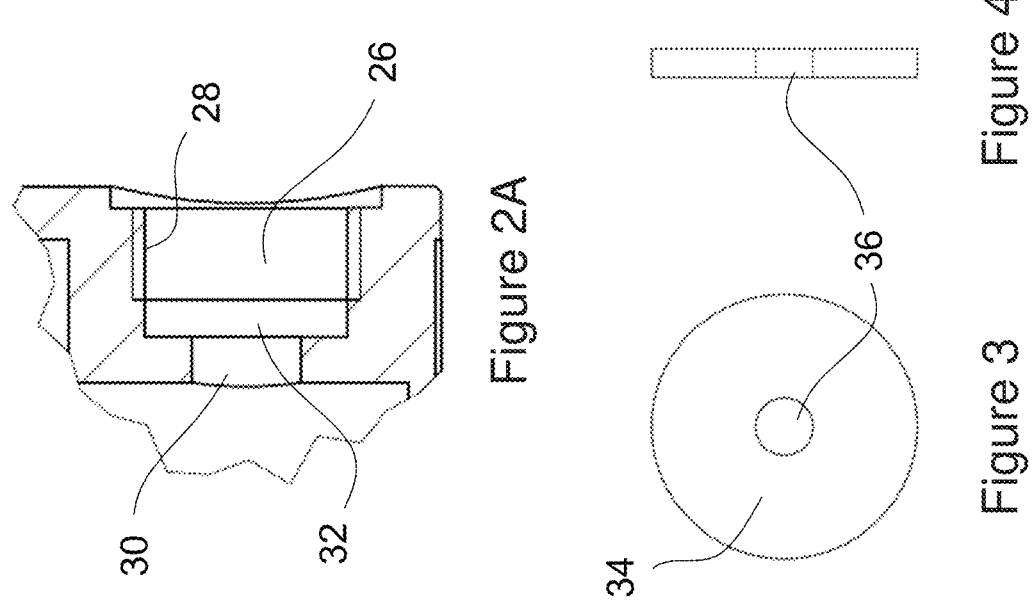
Figure 2A
Figure 3
Figure 4
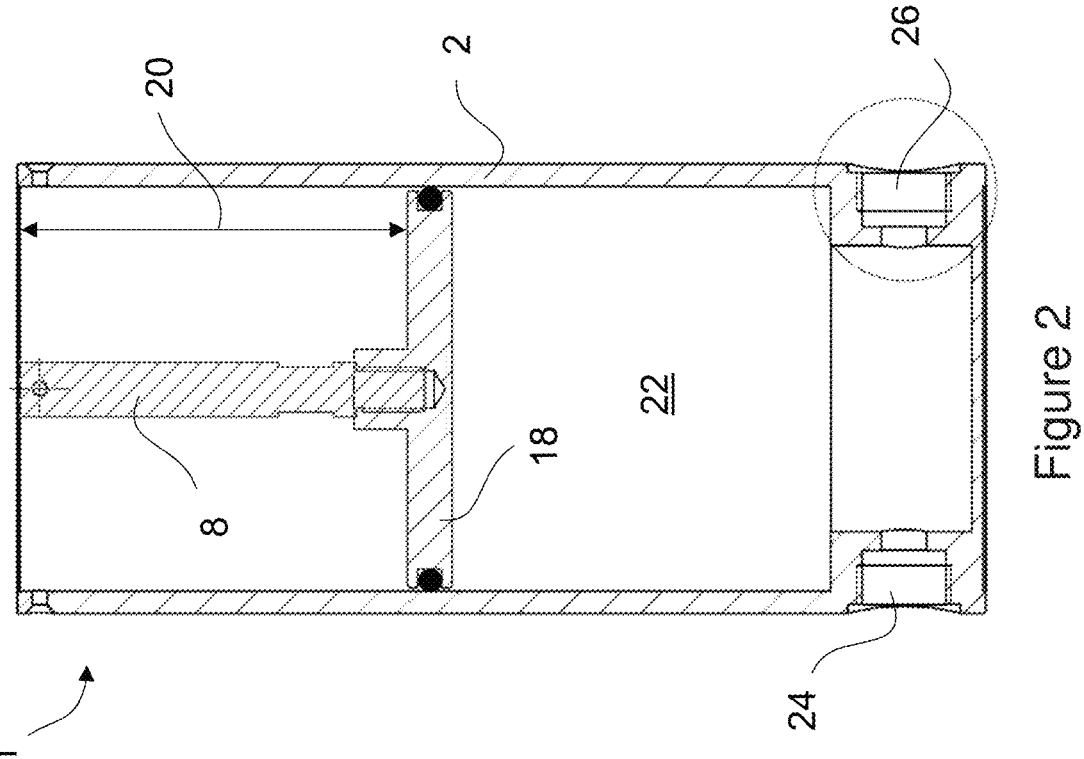
Figure 2

INHALER TESTING APPARATUS

CROSS-REFERENCE TO RELATED APPLICATIONS

This application claims priority to Great Britain Patent Application No. 2210357.6, filed Jul. 14, 2022, and entitled "Inhaler Testing Apparatus", the entire disclosure of which is incorporated herein by reference.

BACKGROUND

The present invention relates to inhaler testing. In particular, the invention relates to a device to improve the consistency and reliability of the testing process.

SUMMARY

Standard tests exist for inhalers, for example to determine the delivered dose or particle size distribution from an inhaler during use. The test process involves simulating a patient inhalation through an inhaler and a collector, typically either a sampling apparatus (in the case of delivered dose) or a cascade impactor (in the case of particle size determination) using a constant flow vacuum pump and a flow controller.

Two known cascade impactors are the Next Generation Impactor (NGI) and Andersen Cascade Impactor (ACI) supplied by Copley Scientific Limited, Nottingham, UK. In both cases, sample/medicament laden air flow passes sequentially through a number of distinct stages of the Impactor. Each stage retains a defined range of particle sizes on a collection plate or cup for further analysis, and the stages are configured and arranged to separate particles, on the basis of particle inertia, into a series of progressively smaller size bands or fractions in the respirable range. The separation broadly corresponds to the particles' likely deposition sites in the respiratory tract. Further details of the operation of the NGI and ACI are available from copleyscientific.com.

A feature of the ACI is that stages are replaceable so that the most appropriate combination of stages (for example stages suitable for generally larger or smaller particle sizes) can be provided for any particular inhaler under test. A further benefit of this adaptable configuration is that stages can be removed entirely so that the impactor can focus on just a subset of the total range of particle sizes.

Abbreviated Impactor Measurement (AIM) is a process where, once the full Aerodynamic Particle Size Distribution (APSD) profile of the product has been established in development using a full-resolution cascade impactor, product batch release testing and quality control applications are possible using simpler but highly sensitive metrics, solely to determine if the product is fit for purpose. Products suitable for AIM include the Fast Screening Impactor (FSI) and Fast Screening Anderson (FSA), both supplied by Copley Scientific. These can be considered essentially simplified or 'abbreviated' versions of the NGI and ACI respectively, comprising fewer stages, and can be used with the same vacuum pump and flow controller as previously described.

The operation of the vacuum pump and flow controller can be adjusted to set a desired pressure drop and duration for the simulated inhalation event, as required for a particular inhaler design. The pressure drop profile ideally takes the form of a square wave, but resistance and dead volume within the overall system results in deviation from the ideal. Variations in the dead volume and resistance change the amount of deviation from the ideal square wave profile, typically by altering the rise-time, and potentially the amount of medicament released, which reduces the reliability and consistency of the testing process.

The present invention serves to overcome or mitigate this problem and improve the consistency and reliability of the testing process.

According to a first aspect of the invention there is provided a volume and resistance compensator device (VRC) as defined in the appended claim 1. Further optional features are recited in the associated dependent claims.

The invention also provides a method of testing inhalers as defined in the appended claim 13. Further optional features are recited in the associated dependent claims.

Different types and designs of collector for use in testing a single inhaler device can have quite different volumes and flow resistances. For example, the more stages are present in a cascade impactor, the greater the 'dead' volume and flow resistance. This means that the flow characteristics (e.g. resistance and rise-time for a simulated inhalation) between a full impactor and an 'abbreviated' impactor can be quite different. The differences can reduce the consistency and reliability of the overall testing process.

For example, the internal volume of the FSI (960 ml) is substantially less than that of the NGI (2025 ml). This volume difference alters the pressure drop profile for a given device, thereby changing the characteristics of the pressure wave which passes through the device and impactor during testing. The flow resistance of the FSI is also considerably lower than that of the NGI, further changing the characteristics of a test. Providing a means to compensate for differences in flow resistance and/or volume help to ensure that an inhaler experiences the same flow characteristics throughout a testing process, regardless of whether a full or 'abbreviated' impactor is used, and remove or minimise variability in inhaler testing.

For a 'passive' dry powder inhaler (DPI) in particular, the activation, dose emission and subsequent dispersion and aerosolisation of a formulation is largely governed by the characteristics of the inhalation event, particularly the rise-time. Any difference in rise-time can result in a significant difference in the aerosolisation and distribution of a medicament, even for a set duration and overall pressure drop, so failing to provide the same flow conditions in a series of tests risks fundamentally changing the performance of the inhaler under test.

The VRC as claimed comprises a variable volume chamber with an inlet and an outlet, at least one of the inlet and outlet being adjustable to vary the resistance to gas flow through the chamber.

The maximum volume of the variable volume chamber may be 1000 ml.

The variable volume chamber may comprise a cylinder and a piston movable, via a shaft, within the cylinder. The piston may seal with one of more interior walls of the chamber to provide a sealed working volume below the piston.

The shaft may comprise a graduated scale to allow a user to monitor the positions of the piston from outside the VRC. A clamp may be provided for selectively fixing the position of the piston within the cylinder as required.

At least one of the inlet and outlet of the VRC may be configured to receive a removable choke plate to reduce the diameter of the flow path through the inlet and/or outlet. The VRC may be provided with two or more choke plates, each choke plate comprising a through hole of a set diameter. A variety of choke plates may be provided. The diameter of the through hole each choke plates is one of 2 mm, 3.5 mm, 4 mm, 4.5 mm, 5.5 mm, 6 mm, 6.5 mm and 8 mm. More than one choke plate of each diameter may be provided. When used without choke plates the VRC may provide negligible flow resistance, or may provide a fixed/known low flow resistance that can be increased by inserting one or more choke plates.

The flow path through the VRC may alternatively be made adjustable via an adjustable valve, such as a needle valve, provided at the inlet and/or outlet. A continuously or infinitely variable flow resistance could be provided.

The volume of the chamber in the VRC may be adjusted independently of the resistance to gas flow through the chamber.

The invention also provides inhaler testing apparatus comprising a collector for connection to an inhaler device, a vacuum pump for generating a gas flow through the collector, a flow controller for controlling the duration of the pressure drop experienced by the collector, and a VRC according to any preceding claim, wherein the volume and resistance compensator device is arranged between the collector and the vacuum pump.

The collector may comprise a sampling apparatus or a cascade impactor. The testing apparatus may further comprise a passive dry powder inhaler connected to the collector.

The invention also provides a method of testing inhalers comprising:

A. Simulating an inhalation event with set parameters through a first collector and measuring the flow resistance and rise-time;

B. Simulating an inhalation event with the same set parameters through a second collector and a volume and resistance compensator device and measuring the flow resistance and rise time;

C. Adjusting a flow resistance and/or working volume of the volume and resistance compensator device until the flow resistance and rise-time measured in step B matches the flow resistance and rise-time measured in step A.

Step A of the method may comprise a first step A1 in which the flow resistance is measured and a second step A2 in which the rise-time is measured. Step B may comprise a first step B1 in which the flow resistance is measured and a second step B2 in which the rise-time is measured.

The method may further comprise the subsequent step of:

D. Testing an inhaler device using the second collector and volume and resistance compensator device as adjusted in step C to acquire data to supplement or complement data acquired from a test of the same inhaler using the first collector.

The method may be performed using the testing apparatus as previously described.

BRIEF DESCRIPTION OF THE DRAWINGS

Practicable embodiments of the invention are described in further detail below with reference to the accompanying drawings, of which:

FIG. 2 shows a cross-section view of the VRC of FIG. 1;

FIG. 2A shows a detail cross-section view of an outlet from the VRC of FIG. 1,

FIG. 3 shows a front view of a choke plate;

FIG. 4 shows a side view of the choke plate of FIG. 3;

DETAILED DESCRIPTION

Figure 1:
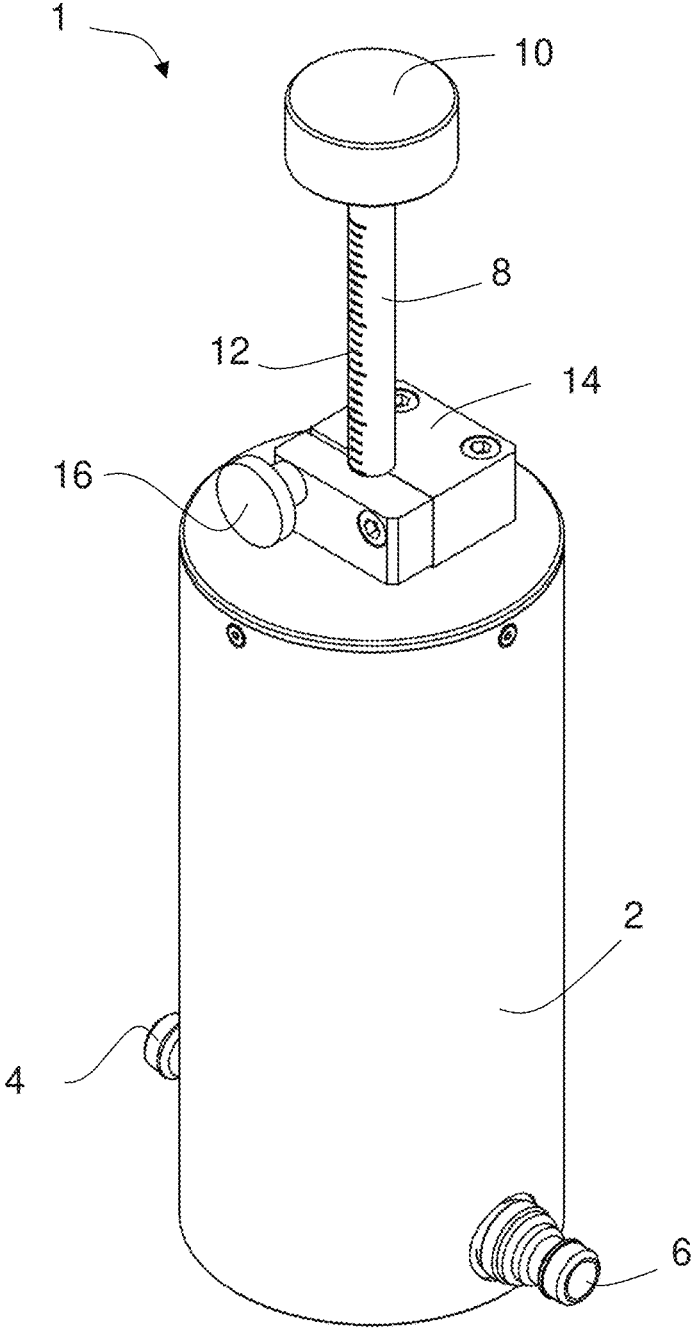
FIG. 1 shows a volume and resistance compensator device (VRC) according to the present invention.

FIG. 1 shows a volume and resistance compensator (VRC) 1 for use in inhaler testing. The VRC 1 comprises a generally cylindrical chamber 2 defining an internal volume with first and second pneumatic connectors 4,6 providing an inlet and outlet respectively. A piston (not shown) is attached to a shaft 8 with a handle 10, and is adjustable vertically to alter the working volume of the chamber 2. A graduated scale 12, indicative of the working chamber volume, is provided on the shaft 8. A two-part clamp 14 is provided to selectively fix the position of the shaft 8, and thus the piston. A screw 16 is provided to loosen or tighten the clamp 14 as required.

A cross section of the VRC 1, including a section of the shaft 8 and the piston 18, is shown in FIG. 2. The position of the piston 18 is adjustable within the chamber 2 to provide an adjustable working volume 22 defined below the piston 18. As shown in FIG. 2 the piston 18 has been moved into the chamber 2 by a distance 20 to reduce the working volume 22 of the chamber from 1000 ml to approximately 600 ml. The first and second pneumatic connectors 4,6 shown in FIG. 1 have been removed from the inlet 24 and outlet 26 of the chamber 2.

Further detail of the outlet 26 is shown in FIG. 2A (the inlet 24 has a similar design). The outlet 26 comprises an internally threaded portion 28 allowing attachment of the second pneumatic connector 6 to the outlet 26, and an outlet aperture 30 from the working volume 22 of the chamber 2. A recess 32 is provided between the outlet aperture 30 and the threaded portion 28 for receiving a choke plate 34 as shown in FIGS. 3 and 4.

A front view of a choke plate 34 is shown in FIG. 3, with a side view shown in FIG. 4. The choke plate comprises a thin disk of brass with a central through hole 36 having a smaller diameter than the outlet aperture 30 of the chamber 2. For example, the outlet aperture 30 may have a diameter of 11 mm, while the hole 36 in the choke plate 34 may have a diameter of 2 mm, 3.5 mm, 4 mm, 4.5 mm, 5.5 mm, 6 mm, 6.5 mm or 8 mm. In use, the choke plate 34 is received in the recess 32 in the outlet 26 (or inlet 24) and is retained in place by a pneumatic connector 4,6 screwed into the threaded portion 28.

The smaller diameter through hole 36 of the or each choke plate 34 compared to the outlet aperture 30 (or inlet aperture) increases the flow resistance through the chamber 2. It will be understood that several different flow resistances could be achieved by selecting just a single choke plate 34, or by using two choke plates 34 with through holes 36 of the same or different diameters in combination.

The tuning of the VRC 1 for a particular testing configuration is an empirical process, essentially performed in two parts. First, the VRC 1 is configured to compensate for the flow resistance of an 'abbreviated' impactor. An example of a testing setup to achieve this is illustrated schematically in FIGS. 5 and 6.

Figure 5:
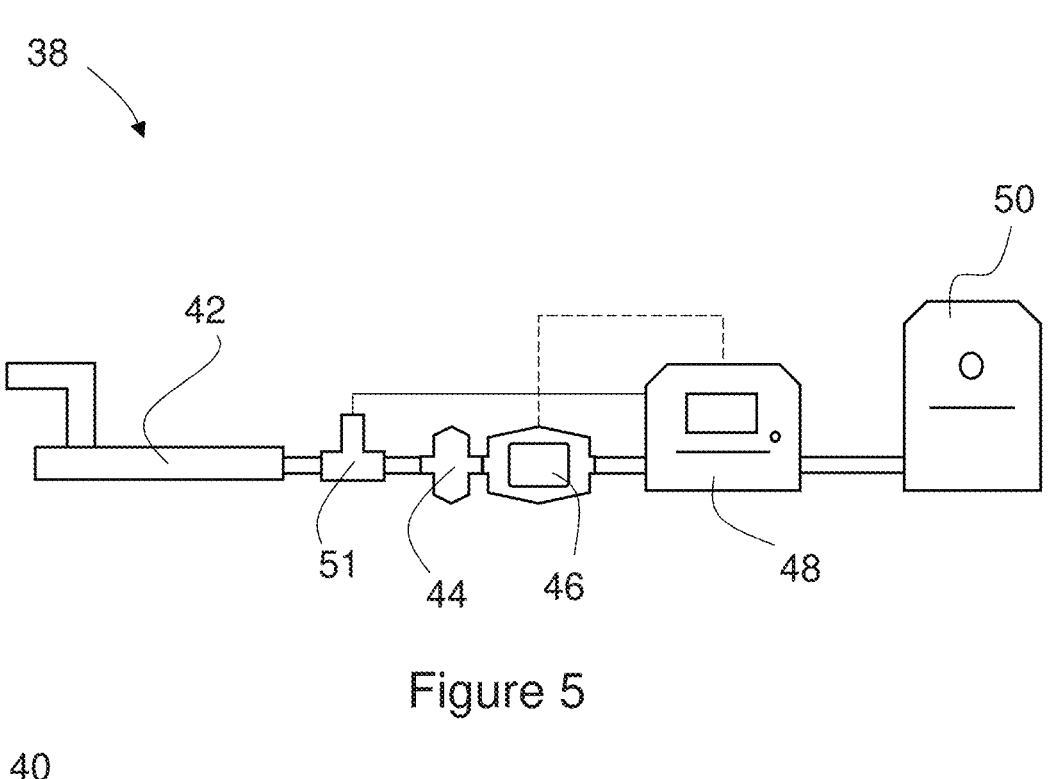
FIG. 5 shows a schematic testing setup for measuring the flow resistance of a cascade impactor.
Figure 6:
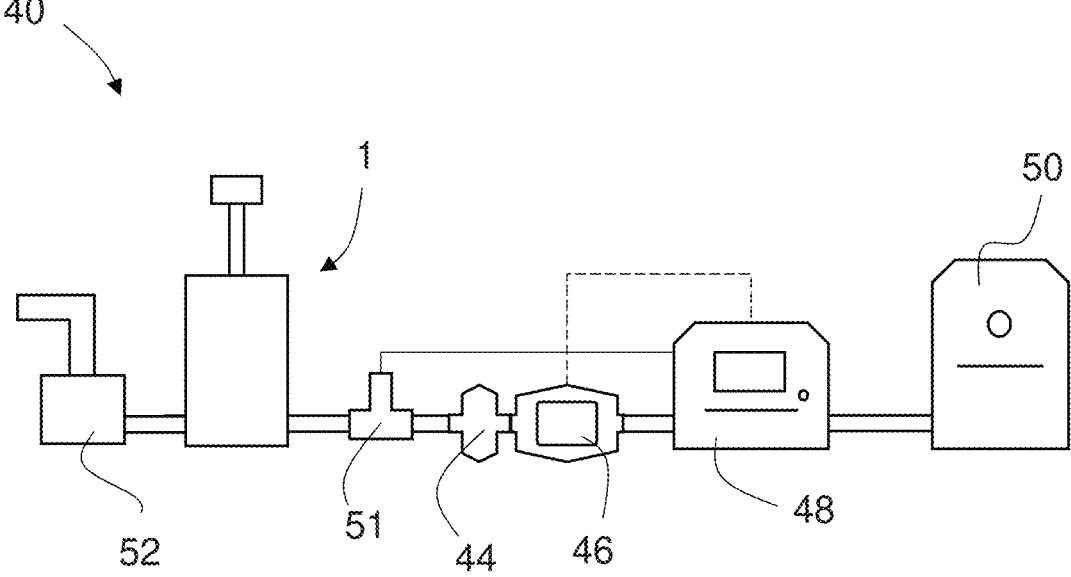
FIG. 6 shows a schematic testing setup for measuring the flow resistance of an abbreviated impactor and the VRC of FIG. 1.

FIG. 5 shows an arrangement of components 38, namely an NGI 42 connected in series with a filter 44, a flow meter 46, a flow controller 48 and a vacuum pump 50. The arrangement 38 allows the flow resistance of a full impactor, such as an NGI 42 to be determined by measuring the pressure drop over the NGI 42 at component 51. FIG. 6 shows a similar arrangement of components 40 but with an FSI 52 and VRC 1 in place of the NGI 42 from FIG. 5. As in the previous example, the flow resistance of the FSI 52 and VRC is determined by measuring the pressure at component 51. By inserting one or more appropriate choke plates 34 in the inlet 24 and/or outlet 26 of the VRC 1 (see FIGS. 2A and 3), the flow resistance through the FSI 52 and VRC 1 can be tuned so that it matches the previously measured flow resistance of the NGI 42.

Figure 7:
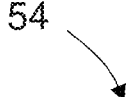
FIG. 7 shows a bar chart of data from the testing setup in FIGS. 5 and 6.
Figure 7:
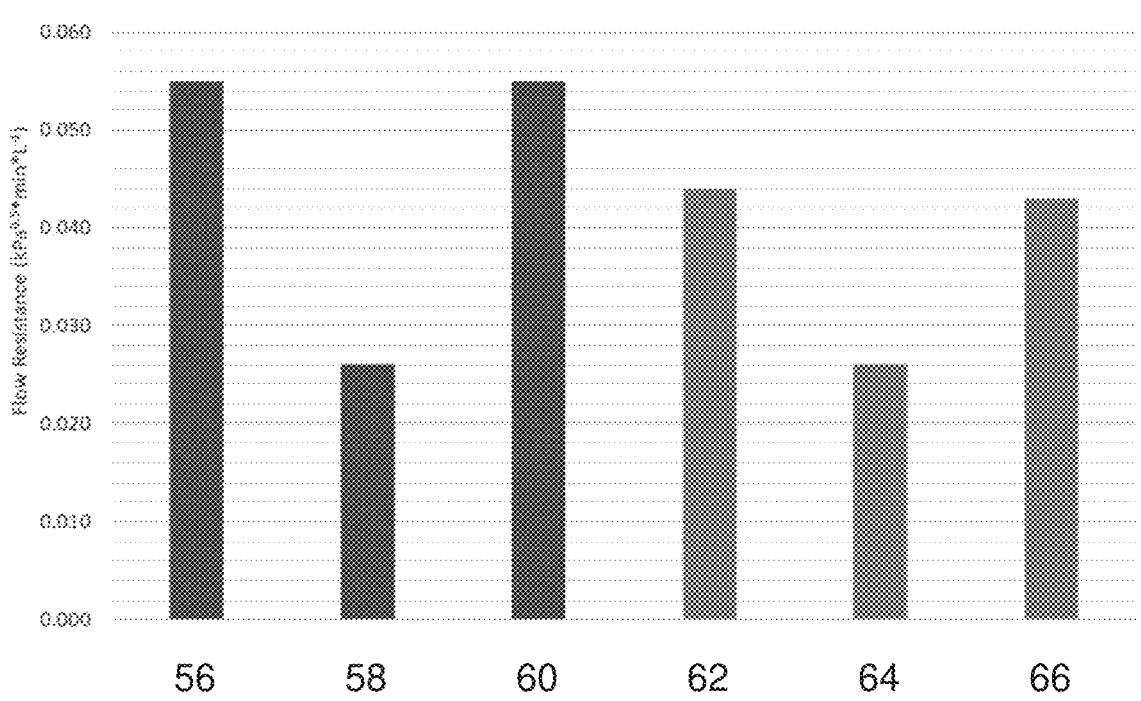

FIG. 7 is a bar chart 54 showing examples of the compensation in flow resistance. The left-hand side of the chart 54 shows a first bar 56 illustrates the flow resistance of the NGI 42 measured in FIG. 5. In contrast, the second bar 58 shows the lower flow resistance measured for an FSI 52 without any compensation. The third bar 60 shows the measured flow resistance for a combination of the FSI 52 with the VRC 1 configured with choke plates 34 having 4.5 mm and 4 mm through holes. The heights of the first bar 56 and third bars 60 match, indicating that this combination of choke plates 34 in the VRC 1 compensates for the lower flow resistance of an FSI 52 compared to an NGI 42.

The right-hand side of the chart 54 shows a fourth bar 62, fifth bar 64 and sixth bar 66 illustrating a similar comparison for an ACI and an FSA. In this instance, the difference in resistance between the ACI and FSA is shown in the contrast between the fourth bar 62 and fifth bar 64. The compensation illustrated in the increased height of the sixth bar 66 is provided by a pair of choke plates 34 having 5 mm through holes in the VRC 1.

It will be understood that the use of choke plates 34 each having a through hole of a fixed diameter helps to ensure that, once set, the flow resistance provided by the VRC 1 is not inadvertently changed. Providing a variable aperture at the inlet 24 and/or outlet 26, for example in the form of a needle valve or similar, could provide faster and simpler adjustment, but with increased risk of variation once set.

Once the VRC 1 has been properly configured to compensate for a reduction in flow resistance, the second step of the setup involves measuring the difference in rise time, and adjusting the volume of the VRC 1 to compensate. The apparatus for this stage is schematically shown in FIGS. 8 and 9.

Figure 8:
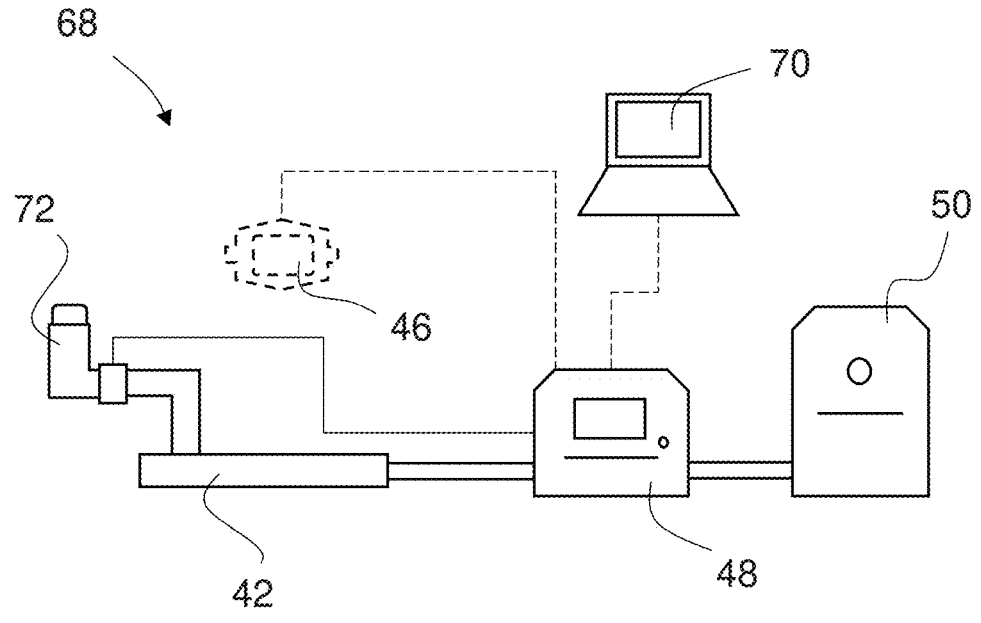
FIG. 8 shows a further schematic testing setup for measuring the rise time with a full cascade impactor and an inhaler device.

FIG. 8 shows an arrangement of components 68, largely similar to that shown in FIG. 5, including an NGI 42, flow meter 46, flow controller 48 and vacuum pump 50. In addition, a personal computer 70 is provided and an inhaler device 72 is connected to an inlet of the NGI 42. The arrangement 68 of FIG. 8 allows the inhalation profile, and specifically the rise-time, to be monitored for a set pressure drop through the inhaler 72 and NGI 42. The flow meter 46 is used in place of the inhaler to ensure that the correct flow conditions are set for the test prior to the rise time being measured with the inhaler attached as shown in FIG. 8.

Figure 9:
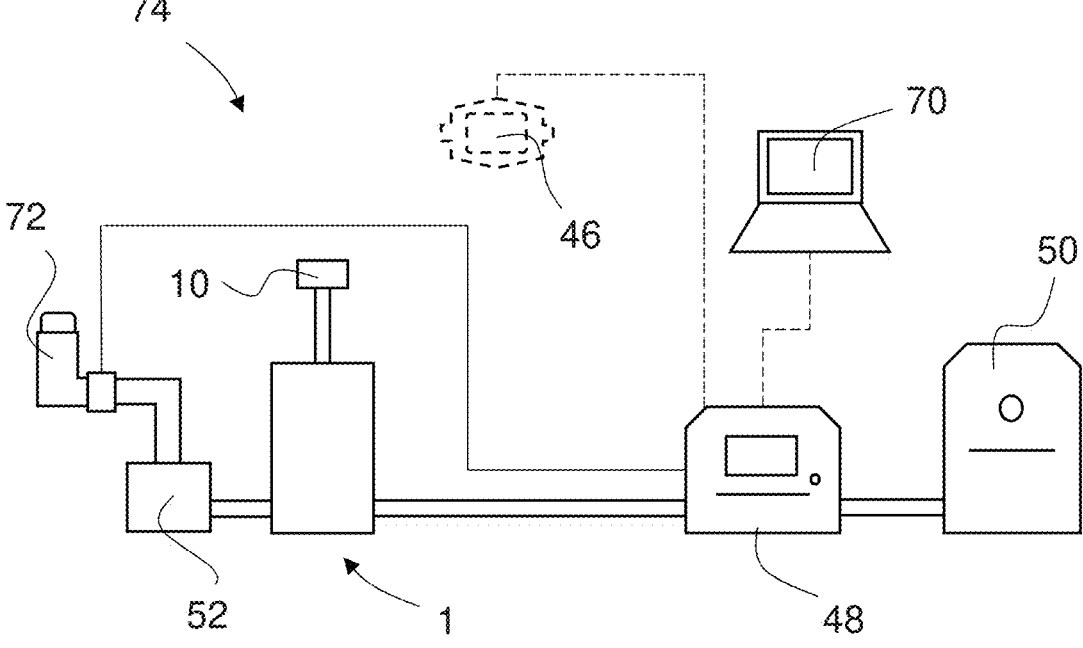
FIG. 9 shows a further schematic testing setup for measuring the rise time with an abbreviated impactor, an inhaler device and the VRC of FIG. 1.

In the arrangement 74 of FIG. 9, the NGI 42 has been replaced by an FSI 52 and a VRC 1. The VRC 1 has already been configured to compensate for the change in flow resistance as described above. The handle 10 of the VRC 1 can be used to adjust the piston position and thus the working volume within the VRC 1 until the rise-time resulting from the combination of the FSI 52 and VRC 1 matches that determined for the NGI 42. The shaft 12 can then be locked in place using the clamp 14 (see FIG. 1) to fix the working volume of the VRC 1 at the required level.

Figure 10:
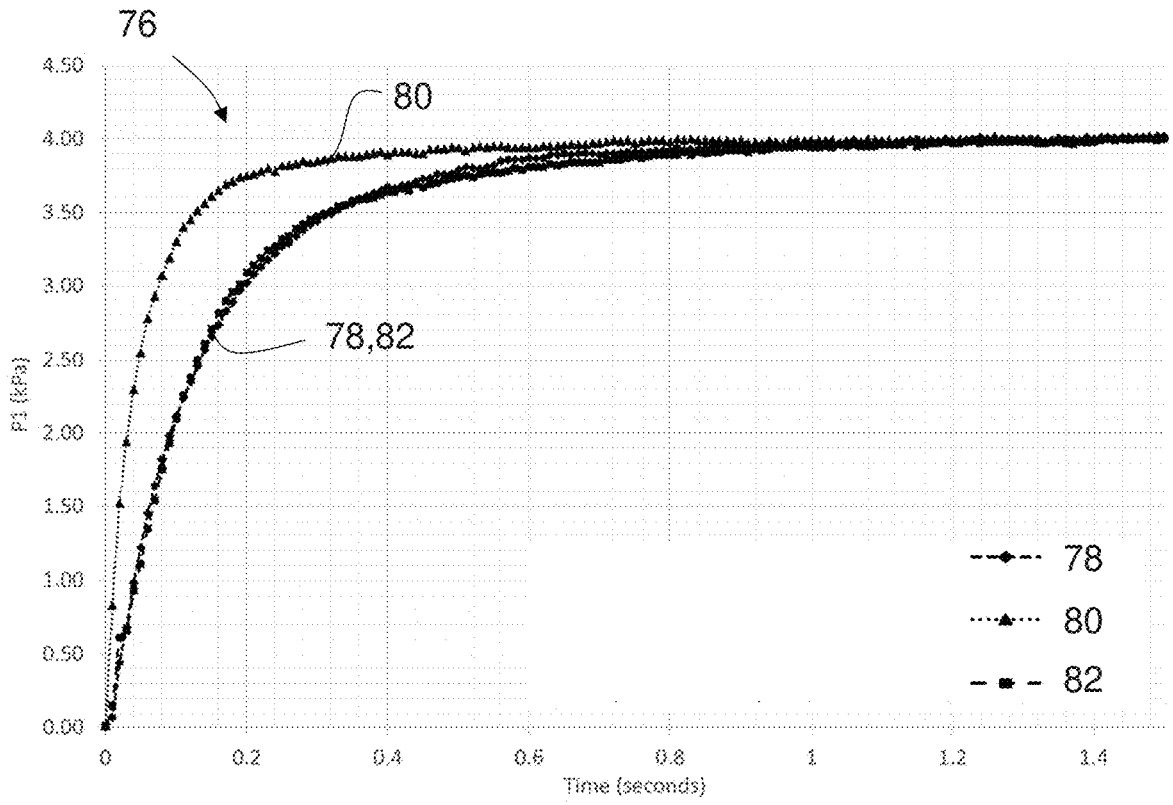
FIGS. 10 and 11 show graphs of data obtained from the further testing setups of FIGS. 8 and 9.
Figure 11:
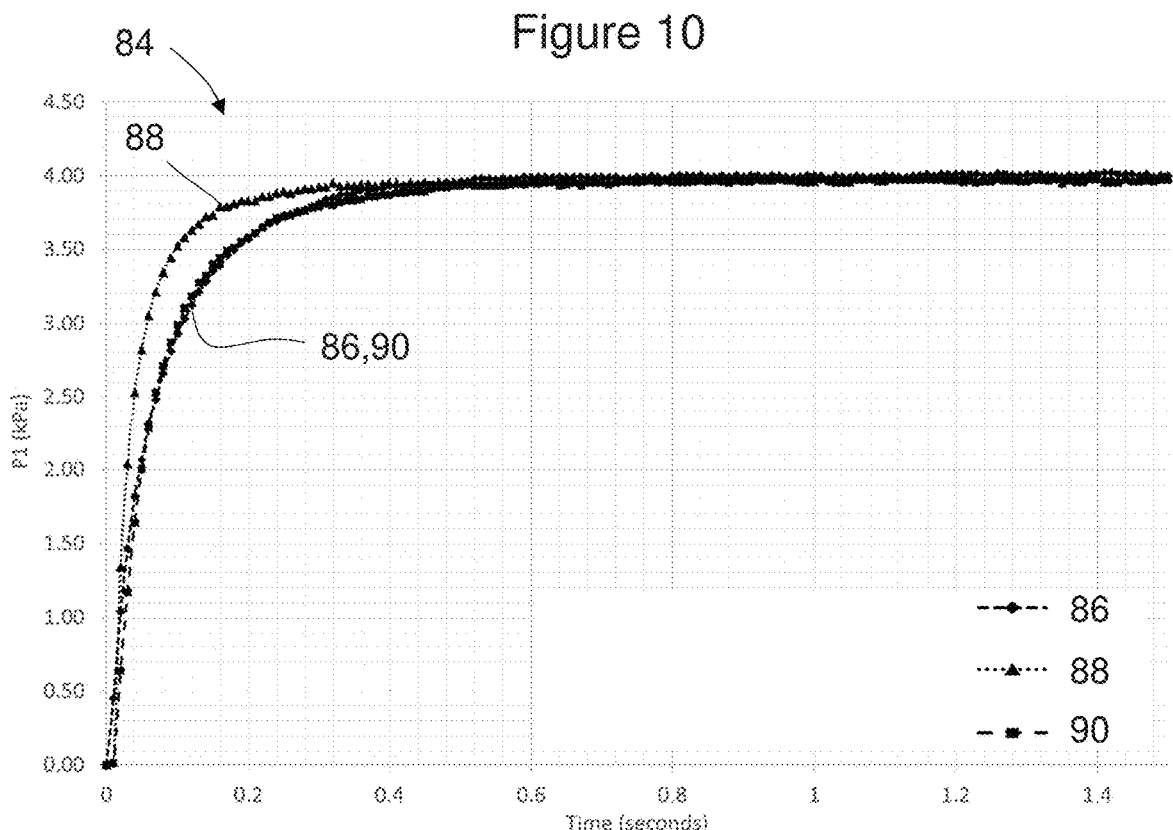

FIG. 10 shows an example graph 76 of pressure against time illustrating the compensation described above for a Turbohaler® inhaler device 72. The plotted data 78,80,82 show, respectively, the pressure profile where an NGI 42 is used in isolation, the profile for an FSI 52 in isolation, and the profile for an FSI 52 and VRC 1 in series. It can be seen that the data plots 78,82 are almost coincident, showing that the shorter rise time for the FSI 52, indicated by the steeper initial gradient of the line 80, has been slowed by the addition and adjustment of the VRC 1 until it matches that determined for the NGI 42 under the same conditions. The VRC 1 in the example has been adjusted to provide a working volume of 600 ml, having previously been configured to compensate for the different flow resistance as described with reference to the left-hand side of chart 54 in FIG. 7. As noted above, the difference between the internal volume of the FSI 52 and the NGI 42 is over 1000 ml, so it can be seen that there is more to matching the rise time than simply adding volume equal to the known difference between two impactors. The volume required in the VRC 1 is less than the difference in volume between the full impactor and abbreviated impactor The graph 84 in FIG. 11 shows similar data plots 86,88,90 for, respectively, an ACI, an FSA, and an FSA in series with an appropriately adjusted VRC 1. In this example, the VRC 1 has been adjusted to provide a smaller working volume of 300 ml, having previously been configured to compensate for the different flow resistance as described with reference to the right-hand side of chart 54.

The VRC 1 is effective in matching both the flow resistance and rise-time of a full impactor with an abbreviated impactor. It allows independent adjustment of flow resistance and volume, to compensate for differences between a wide range of different test setups. Each of the resistance and volume can be reliably set, once adjusted for a particular cascade impactor, but the VRC 1 remains adjustable for subsequent use with different cascade impactors.

While the invention is described above with specific reference to particle size determination, it should be appreciated that the described volume and resistance compensator (VRC) would be equally suitable for compensating for differences in resistance and volume experienced in different testing setups, for example with different sampling apparatus for delivered dose testing or for other collectors within a similar overall setup.

Various other uses and minor modifications would also be apparent to a skilled reader. As such, it is emphasised that the forgoing description is provided by way of example only, and is not intended to limit the scope of protection as defined with reference to the appended claims.

The invention claimed is:

1. A volume and resistance compensator device for use in inhaler testing, the volume and resistance compensator device comprising a variable volume chamber with an inlet and an outlet, at least one of the inlet and the outlet being adjustable to vary a resistance to gas flow through the variable volume chamber, wherein the variable volume chamber comprises a cylinder and a piston movable, via a shaft, within the cylinder, wherein at least one of the inlet and the outlet is configured to receive a removable choke plate to reduce a diameter of a path of the gas flow through at least one of the inlet and the outlet, and the volume and resistance compensator further comprising at least one choke plate comprising a through hole of a set diameter.

2. The volume and resistance compensator device according to claim 1, wherein the variable volume chamber has a maximum volume of 1000 ml.

3. The volume and resistance compensator device according to claim 1, wherein the shaft comprises a graduated scale.

4. The volume and resistance compensator device according to claim 1, further comprising a clamp for selectively fixing a position of the piston within the cylinder.

5. The volume and resistance compensator device according to claim 1, comprising two or more choke plates, each choke plate comprising a through hole of a set diameter.

6. The volume and resistance compensator device according to claim 5, wherein the set diameter of the through hole in each choke plate is one of 2 mm, 3.5 mm, 4 mm, 4.5 mm, 5.5 mm, 6 mm, 6.5 mm and 8 mm.

7. The volume and resistance compensator device according to claim 1, wherein a volume of the chamber can be adjusted independently of the resistance to gas flow through the chamber.

8. An inhaler testing apparatus comprising a collector for connection to an inhaler device, a vacuum pump for generating a gas flow through the collector, a flow controller for controlling a duration of a pressure drop experienced by the collector, and the volume and resistance compensator device according to claim 1, wherein the volume and resistance compensator device is arranged between the collector and the vacuum pump.

9. The inhaler testing apparatus according to claim 8, wherein the collector comprises a sampling apparatus or a cascade impactor.

10. The inhaler testing apparatus according to claim 9, further comprising a passive dry powder inhaler connected to the collector.

11. A method of testing inhalers comprising:

A) simulating an inhalation event with set parameters by flowing gas through a first collector and measuring a flow resistance and rise-time;

B) simulating the inhalation event with the same set parameters by flowing gas through a second collector and a volume and resistance compensator device and measuring a flow resistance and rise time;

C) adjusting at least one of the flow resistance and a working volume of the volume and resistance compensator device until the flow resistance and rise-time measured in step B matches the flow resistance and rise-time measured in step A; and D) testing an inhaler using the second collector and volume and resistance compensator device as adjusted in step C to acquire data to supplement or complement data acquired from a test of the same inhaler using the first collector.

12. The method of testing inhalers according to claim 11, wherein step A comprises a first step A1 in which the flow resistance is measured and a second step A2 in which the rise-time is measured.

13. The method of testing inhalers according to claim 11, wherein step B comprises a first step B1 in which the flow resistance is measured and a second step B2 in which the rise-time is measured.

14. The method of testing inhalers according to claim 11, wherein the method is performed using an inhaler testing apparatus comprising a collector for connection to an inhaler device, a vacuum pump for generating a gas flow through the collector, a flow controller for controlling a duration of a pressure drop experienced by the collector, and a volume and resistance compensator device comprising a variable volume chamber with an inlet and an outlet, at least one of the inlet and the outlet being adjustable to vary a resistance to the gas flow through the variable volume chamber, wherein the volume and resistance compensator device is arranged between the collector and the vacuum pump.

15. The method of testing inhalers according to claim 14, wherein the variable volume chamber comprises a cylinder and a piston movable, via a shaft, within the cylinder, wherein at least one of the inlet and the outlet is configured to receive a removable choke plate to reduce a diameter of a path of the gas flow through at least one of the inlet and the outlet, and the volume and resistance compensator further comprising at least one choke plate comprising a through hole of a set diameter.

\* \* \* \* \*